US006302855B1

United States Patent
Lav et al.

(10) Patent No.: US 6,302,855 B1
(45) Date of Patent: Oct. 16, 2001

(54) MEDICAL APPARATUS FOR USE BY A PATIENT FOR MEDICAL SELF TREATMENT OF DIABETES

(75) Inventors: Steffen Lav, Brønshøj; Jens Aage Munk, Stenløse; Brian Ritsing, Lyngby, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/312,796

(22) Filed: May 17, 1999

Related U.S. Application Data (60) Provisional application No. 60/087,187, filed on May 29, 1998.

(30) Foreign Application Priority Data

May 20, 1998 (DK) .............................................. 1998 00714

(51) Int. Cl.⁷ ........................................................ A61B 5/00
(52) U.S. Cl. .............................................. 600/584; 604/71
(58) Field of Search ................................ 604/66, 50, 65, 604/67, 93, 131, 71; 600/181, 183, 573, 583, 584

(56) References Cited

U.S. PATENT DOCUMENTS 5,489,414 * 2/1996 Schreiber et al. ...................... 422/64
5,665,065 * 9/1997 Colman et al. ......................... 604/66

* cited by examiner

*Primary Examiner*—Robert L. Nasser
*Assistant Examiner*—Pamela Wingood (57) ABSTRACT

The invention relates to an apparatus for self-treatment of diabetes. The apparatus is particularly advantageous by comprising a plurality of devices each of which has its own dedicated function corresponding to a number of acts which a diabetic must perform on himself. The individual devices are mutually interconnectible, and the combination comprises at least a body fluid analyzer and a dosing apparatus for administering a predetermined dose of insulin to the patient. Each of the devices may be provided in several sizes so that the user himself may combine the relevant devices of the relevant size with respect to the current need. This reduces the risk of forgetting parts of the equipment, and the confidence of using the equipment is enhanced because it is evident to the user that it is a complete apparatus consisting of unified parts.

26 Claims, 9 Drawing Sheets

MEDICAL APPARATUS FOR USE BY A PATIENT FOR MEDICAL SELF TREATMENT OF DIABETES

CROSS-REFERENCE TO RELATED APPLICATIONS

This application claims priority under 35 U.S.C. 119 of Danish application PA 1998 00714 filed May 20, 1998, and of U.S. Provisional application No. 60/087,187 filed on May 29, 1998, the contents of which are fully incorporated herein by reference.

This invention comprises a medical apparatus for use by a patient for medical self treatment of diabetes, the treatment including a first operation and at least a second operation, the apparatus comprising a first device for performing the first operation and a second device for performing the second operation.

For a number of years it has been possible to purchase various devices for the treatment of diabetes, e.g. for injecting insulin, for measuring blood sugar (such a device is referred to as BGM below), for withdrawing blood samples, and other accessories, the purpose of which is to enable the patient to nurse his disease discretely and with a high standard of hygiene. Many diabetic patients are elderly people who can easily get insecure with respect to the medical equipment, but also many young people need to assure themselves that the equipment is in order, i.e. that everything is there. Or as one must often say to one's children: You have got it all, haven't you?

It has also been attempted to build several of the necessary devices together to a single integral unit, see e.g. U.S. Pat. No. 5,536,249. This is not the ideal solution either, because such multi-functional devices are normally difficult to operate. A patient holding a gadget in his hand may not be entirely secure and convinced that he has set the apparatus to precisely the function to be performed by means of programmable computers. The more complicated the apparatus, the greater the risk of malfunction, meaning that two such multi-functional devices should actually be on hand.

The individual devices may be arranged for various respective functions relevant to the treatment of diabetes, such as: a lancet device, a body fluid analyzer, and a dosing apparatus for administering a predetermined dose of medication to the patient. Further, there are a number of other aids which the diabetic patient uses, e.g. test strips for the blood analyzer, napkins for wiping off blood, extra insulin carpoule, glucose tablets, waste containers, etc.

It is not common to build two individual devices together, as manufacturers within the field have tended to specialize in a single device. However, U.S. Pat. No. 4,469,110 discloses a lancet device and a simple form of BGM (the calorimetric measuring principle) which may be mutually interconnected to a single portable unit.

The object of the invention is to make the individual devices physically interconnectible with a view to optimizing self-treatment of diabetes.

Another object is to construct the individual interconnectible devices such that the optimum treatment is as independent as possible of the specific situation of the user.

A further object of the invention is to provide an apparatus of the present type for self-treatment of diseases, where, on one hand, the user is certain that he has all the devices which will be relevant for a future span of time, and on the other hand, is confident about the use of the apparatus.

The object is achieved by making at least a BGM and an insulin doser interconnectible to a single device. Precisely this combination promotes the insulin treatment, as it will be more obvious to the user to adjust the insulin balance if he has just measured his blood sugar; or if the user knows that he is soon to take insulin, it will be more obvious to check the blood sugar content first. This combination departs from the common view where these two devices do not belong together, presumably because the manufacturers have specialized within either the one or the other device.

The invention is not restricted to the combination of BGM and insulin doser devices, as these devices may be coupled with other devices which are used in the insulin treatment.

The fact that the individual devices may be combined so that the apparatus covers precisely a given need, means that the apparatus takes up as little space is possible, it being simultaneously easy, even for visually handicapped users, to identify each individual device, so that they will be quite confident that the units fit together. When the devices fit together physically, the users will also be confident that, e.g., the measuring units used are the same. This improves the confidence of using the apparatus of the invention.

A blood sugar measuring device normally comprises a temperature monitoring device, and in a preferred embodiment the latter device is arranged such that it is close to the insulin carpoule when the blood fluid analyzer and the insulin injecting device are coupled together according to the invention. The temperature monitoring device may hereby be used not only for adjusting the blood sugar measurement, but may also be used to warn the user if the apparatus has been in a too hot environment and the insulin has been destroyed. This is a particular technical advantage by combining precisely the BGM and the doser.

In addition to the possibility of coupling various devices together as needed, it is also possible for one or more of the devices to have several sizes. This may be relevant particularly for the insulin injecting device and for a storage device, enabling the user to combine precisely the devices of the relevant size which will be needed in a given situation, such as an evening party, a working day, a weekend or on a holiday. The optimum treatment achieved by the apparatus of the invention is thereby more independent of the specific situations in which the user may be, and in which the treatment would be inconvenient with the known separate devices.

In the invention, the devices have their own easily recognisable functions which are well-known to the user. The invention does not exclude the use of others of the user's older (i.e. well-known and secure) devices in combination with the invention, which, however, inspires the user to extend his self-treatment apparatus with units which fit together according to the invention.

In conclusion, it is an essential feature of the invention that the stated advantages are of great importance to the user's perception of and habituation to regarding BGM measurement and insulin dosing as closely unified actions, which results in a better self-treatment.

FIG. 9 shows a third combination of the items presented in FIGS. 1–6, In the following an embodiment of the invention will be described in detail with reference to FIGS. 1–6. FIGS. 7–11 show some useful combinations which illustrate the use of the invention.

The invention also opens up the possibility of a wide variety of combinations as each of said devices may be provided in several sizes. The preferred insulin dosing device may e.g. be replaced by two insulin injection pens of half the size, and a waste container may be inserted instead of one of these pens.

Figure 1:
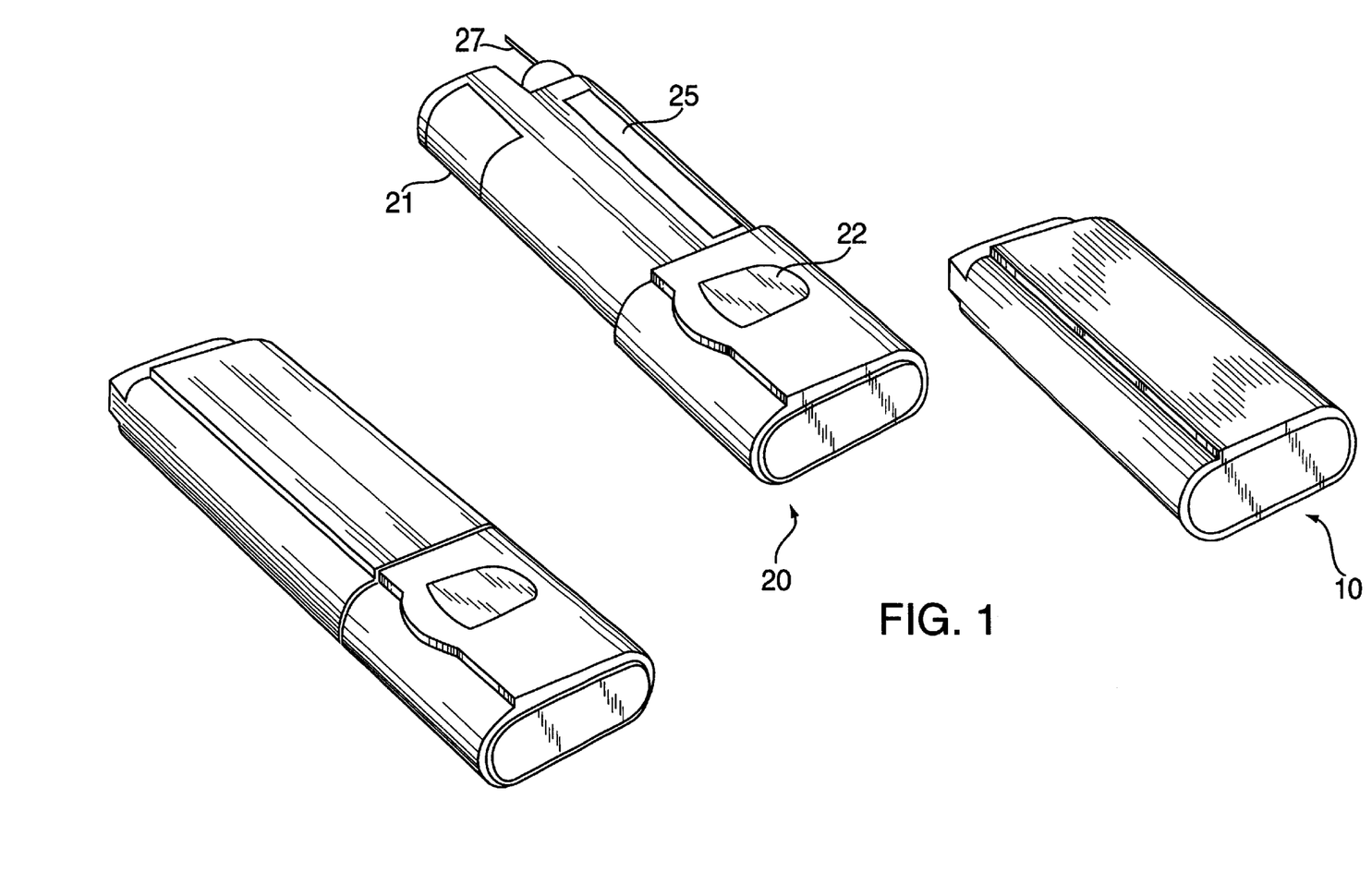
FIG. 1 shows a prior art doser with a conventional cap.

FIG. 1 shows a doser 20 and a cap 10. The doser 20 comprises a turning wheel 21 for adjusting, either electronically or manually, the level/amount of medication to be administered, and a display 22 that shows the currently selected amount of medication to be administered. The doser 20 has processing means and storage facilities, like a CPU and RAM, for storing data, like the time, date and amount of medication of the last couple of administrations. This information can be shown in the display 22 at request. The doser 20 further comprises a carpoule (not shown) that contains the medication, and is fitted with a needle 27 through which the medication is administered. The doser 20 has a transparent window 25 so that the amount of medication left in the carpoule can readily be identified. The cap 10 can be fitted to the doser 20 so that one single compact unit and protection of the doser 20, needle 27, etc. is obtained.

Figure 2:
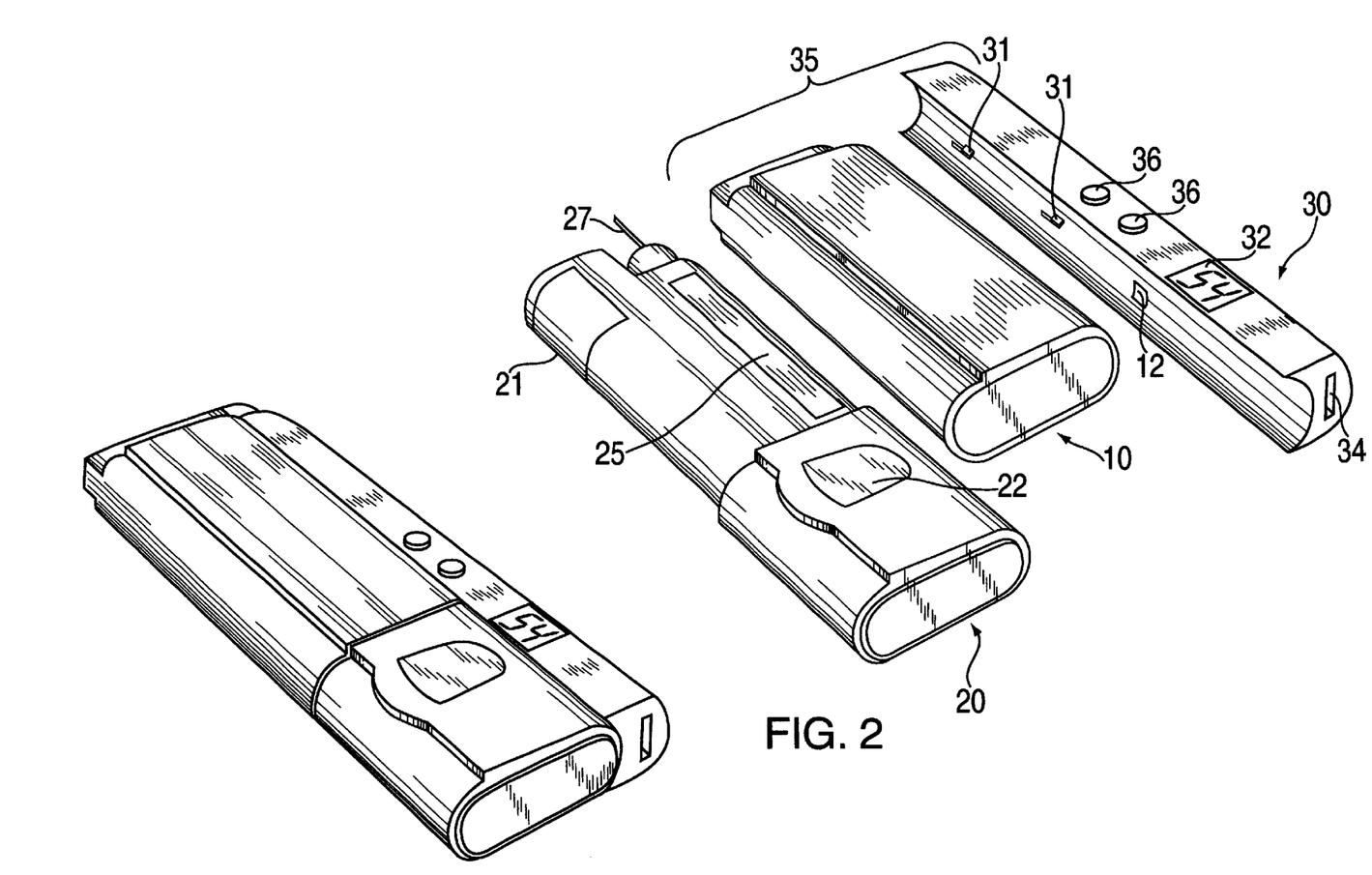
FIG. 2 shows a doser and a cap with a BGM attached.

FIG. 2 shows a doser 20 which corresponds to the doser in FIG. 1. Also shown is a cap part 10, and a BGM 30. The invention is based on the circumstance that the doser 20 and the BGM 30 should be used together very frequently, one embodiment of the invention might be a cap where the BGM 30 is an integral part. Another embodiment, which is the one shown in FIG. 2 and described later, could be one where the BGM 30 can be fitted removable by the locking means 31 to the cap part 10 in such a way that a single unit 35 serving as a cap is formed. This has the advantage that when the cap unit 35 is fitted to the doser 20, one set of parts associated functionally can be obtained in a very compact and convenient form. Another option available to the user by this arrangement is that if in special cases the BGM 30 is not needed in a given situation, the user can simply leave the BGM 30 at home, thereby reducing and keeping the size of the device to an absolute minimum.

The BGM 30 has means 34 for inserting test strips 52 (not shown, see FIG. 4) containing a sample of blood, for analysis by the BGM 30 by operating the buttons 36. The result of the analysis is shown in the display 32.

The cap unit 35 may also be provided with a temperature sensor 12, which determines the outside temperature during operation of the BGM 30. This temperature is needed for the calibration of the BGM 30 prior to the analysis of a blood sample. The temperature sensor 12 could be placed close to the carpoule, so that an additional benefit, apart from being used in the calibration, is achieved when the cap unit 35 is fitted over the doser 20. In this location the sensor 12 can monitor the temperature of the medication contained inside the carpoule. This additional feature is very convenient if the medication is sensitive to temperature and could be ruined or damaged if the temperature of the medication is outside a given interval. Thus the BGM 30 could notify the user if the medication has been exposed to a harmful temperature, which improves the user's safety, especially in the case of the medication being insulin, where the consumption/injection of damaged medicine could cause life-threatening situations.

Figure 3:
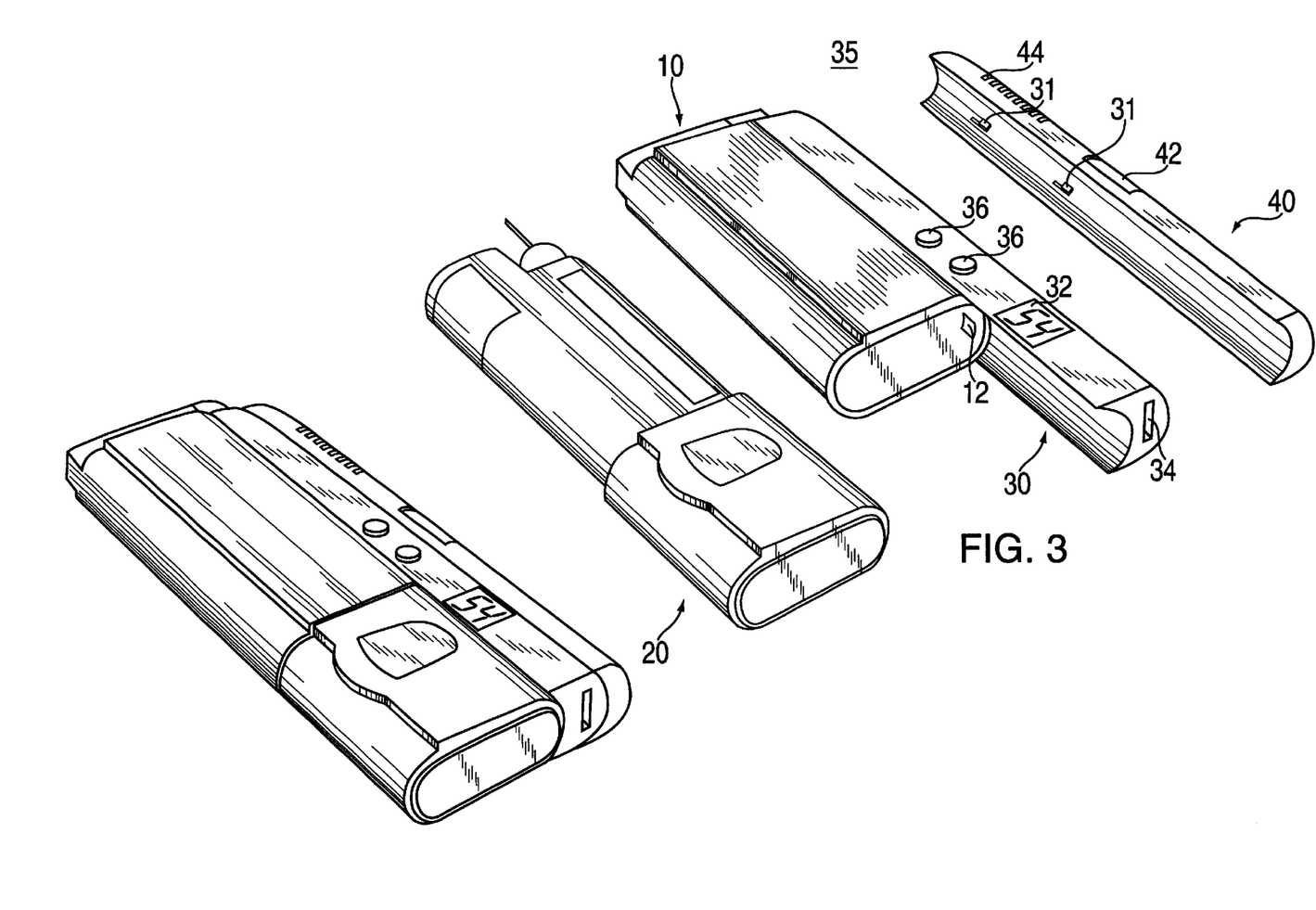
FIG. 3 shows a doser and a cap with a BGM and a lancet device attached.

FIG. 3 shows a doser 20 and a cap unit 35, preferably comprising the cap 10 and the BGM 30, like the cap unit in FIG. 2, but with the additional feature of having a lancet device 40 removably attached to the BGM 30 by the locking means 31. This lancet device 40 is used by first loading the lancet device through the grip 44 and then pressing the button 42, which releases the lancet, piercing the skin, so that a blood sample can be obtained. With this inclusion the lancet device 40 is always at hand. This has the advantage that a lancet device 40 always is available, for taking a blood sample and applying it to a test strip 52. The test-strip 52 can then be inserted via the means 34 into the BGM 30, which will start analyzing the blood sample and, after completion of the analysis, will show the result in the display 32. It is very useful to have the BGM 30 and the lancet device 40 attached together in one compact unit, since a BGM 30 would not normally be used without the lancet device 40, thereby avoiding the fuss and uncertainty of using multiple devices of perhaps different makes. On the other hand, if the user already has a lancet device and is accustomed to and familiar with the use of this particular lancet device, he can still use this original lancet device and just use the remaining items, which will be a compact set consisting of a doser 20 and a BGM 30; The cost will be reduced hereby.

Figure 4:
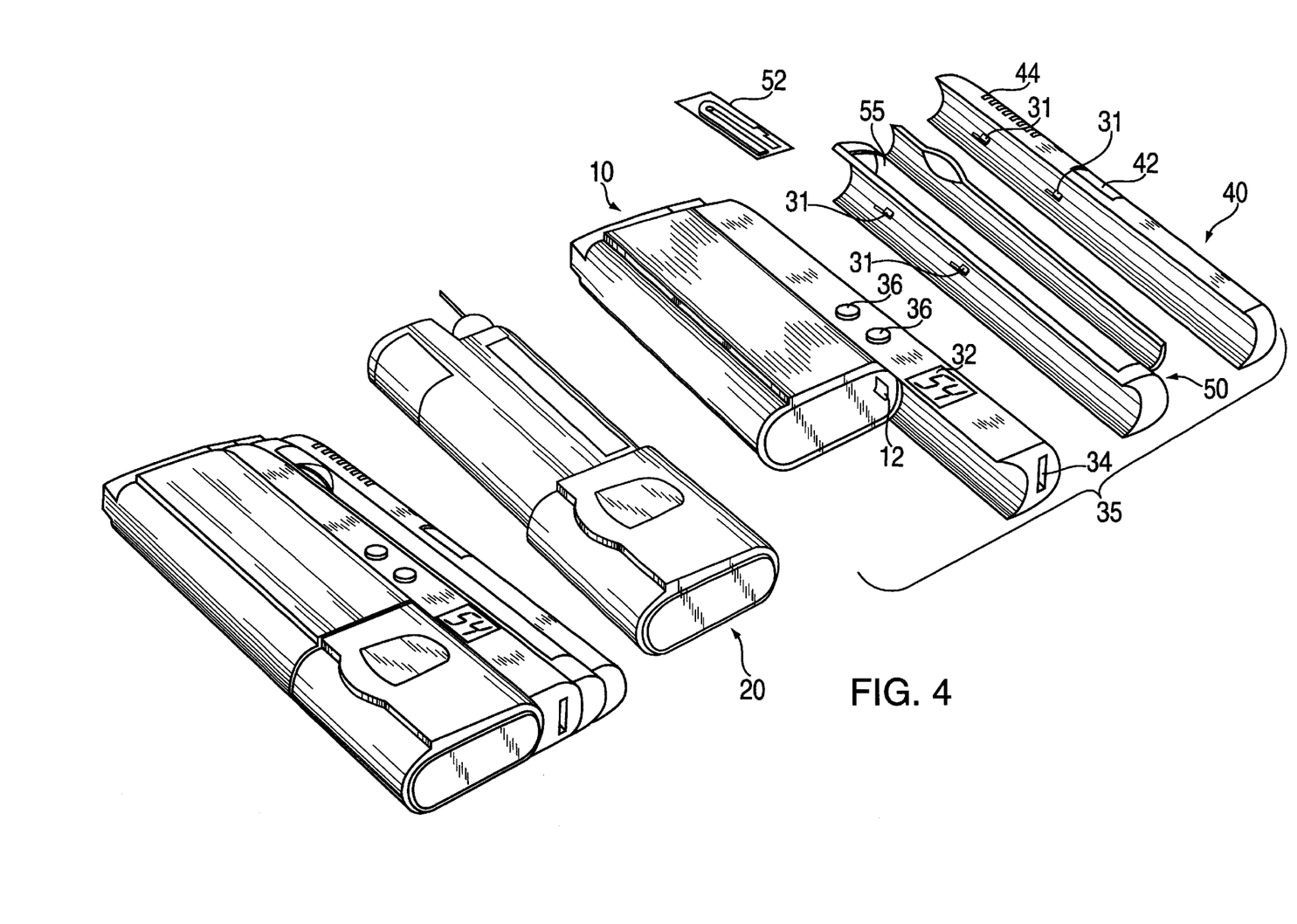
FIG. 4 shows a doser and a cap with a BGM, a lancet device and a container for test strips attached.

FIG. 4 shows a doser 20 and a cap unit 35 from FIG. 3, but where the additional feature of a test strip container 50 for the safe keeping/storing of test-strips 52 in the space 55 can be added/attached through locking means 31. With this addition a test strip 52 will always be available. This addition further strengthens the use of the compact unit obtained, when the cap unit 35 is fitted to the doser 20. Now the user can either have a single compact unit where all the means for taking and analysing a blood sample are available, or have an even smaller compact unit with just the items (e.g. doser 20 with a BGM 30 plus either a test strip container 50 or a lancet) that are needed, depending on the specific situation.

Figure 7:
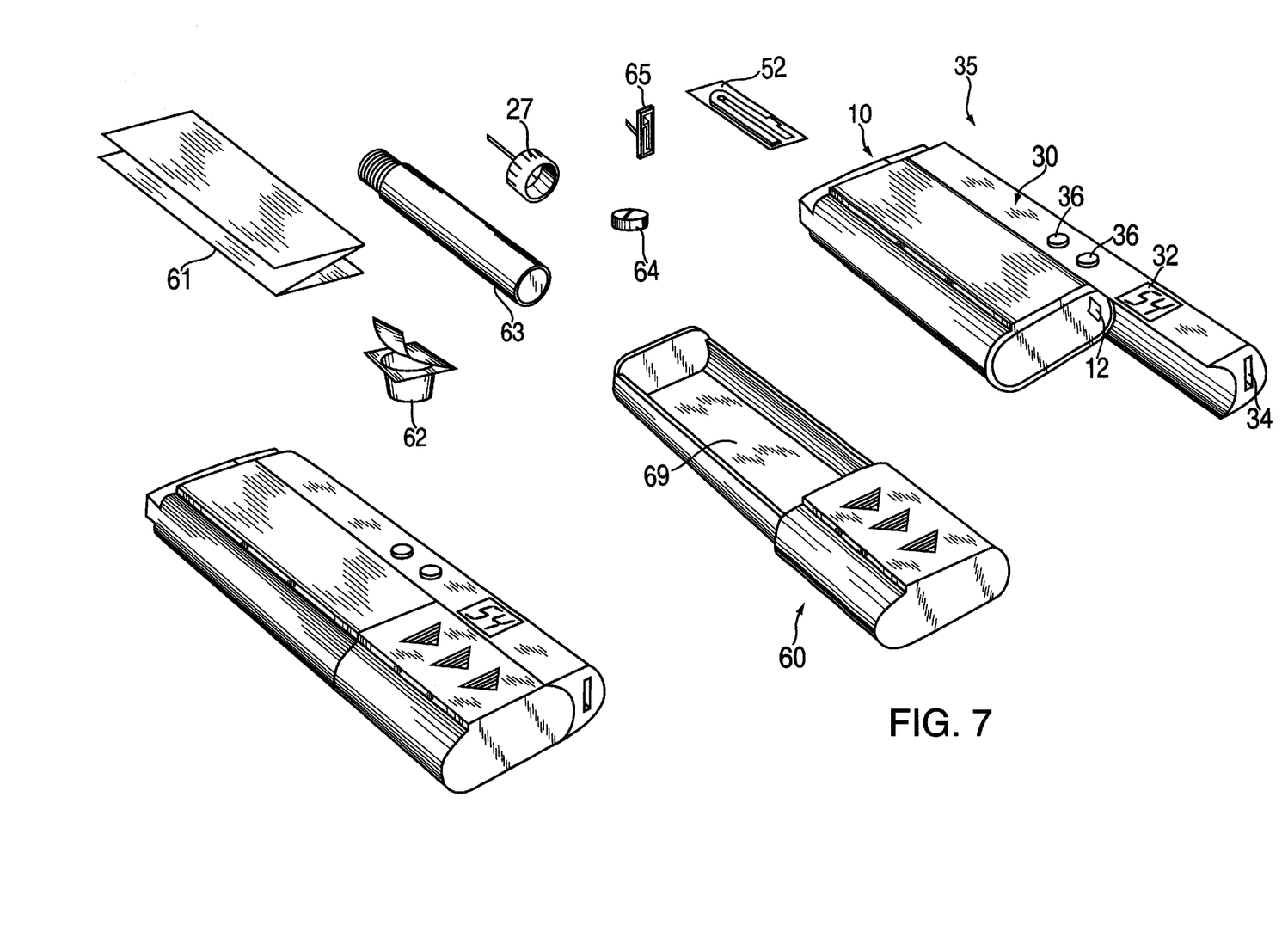
FIG. 7 shows a first combination of the items presented in FIGS. 1–6.
Figure 8:
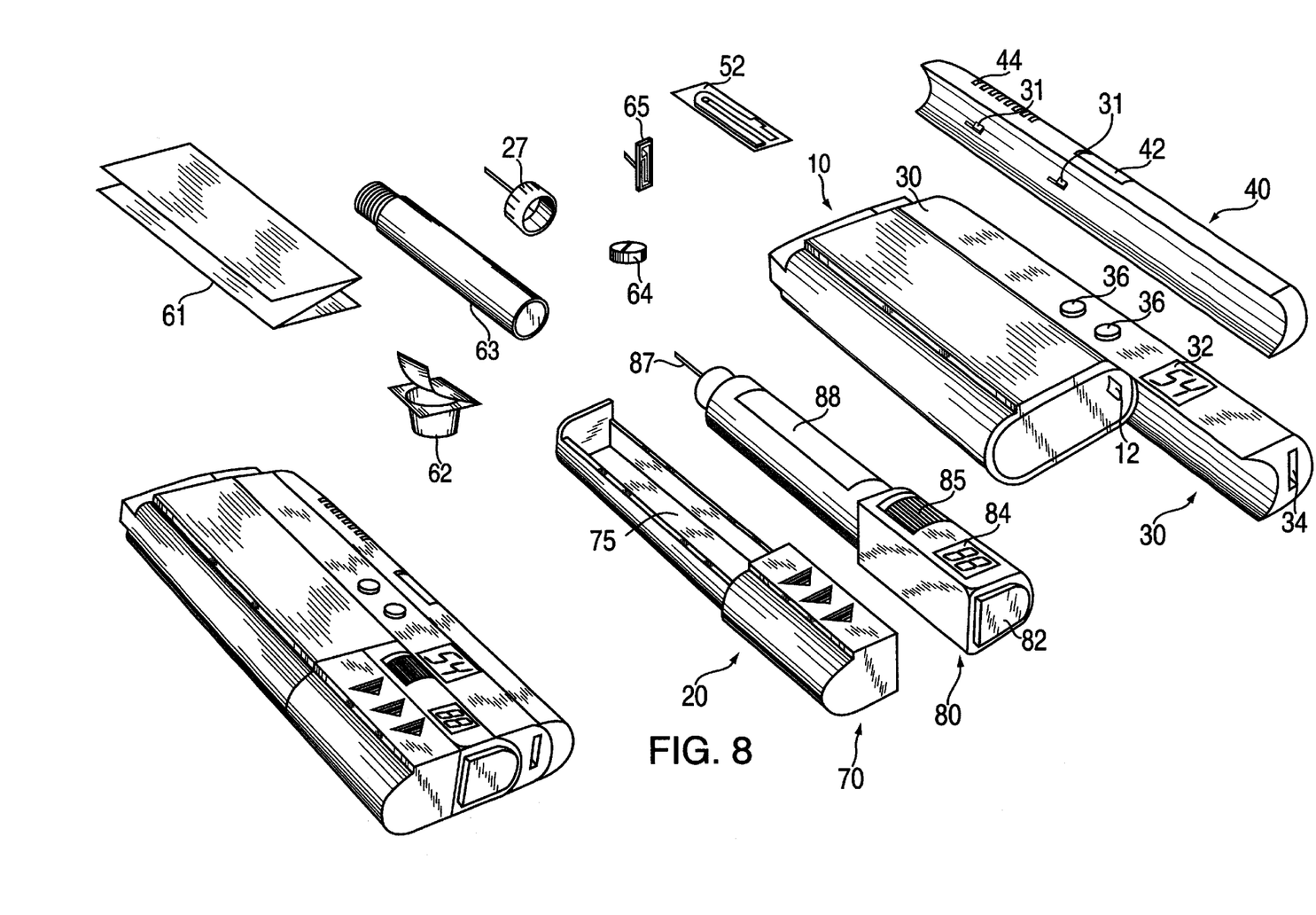
FIG. 8 shows a second combination of the items presented in FIGS. 1–6.
Figure 9:
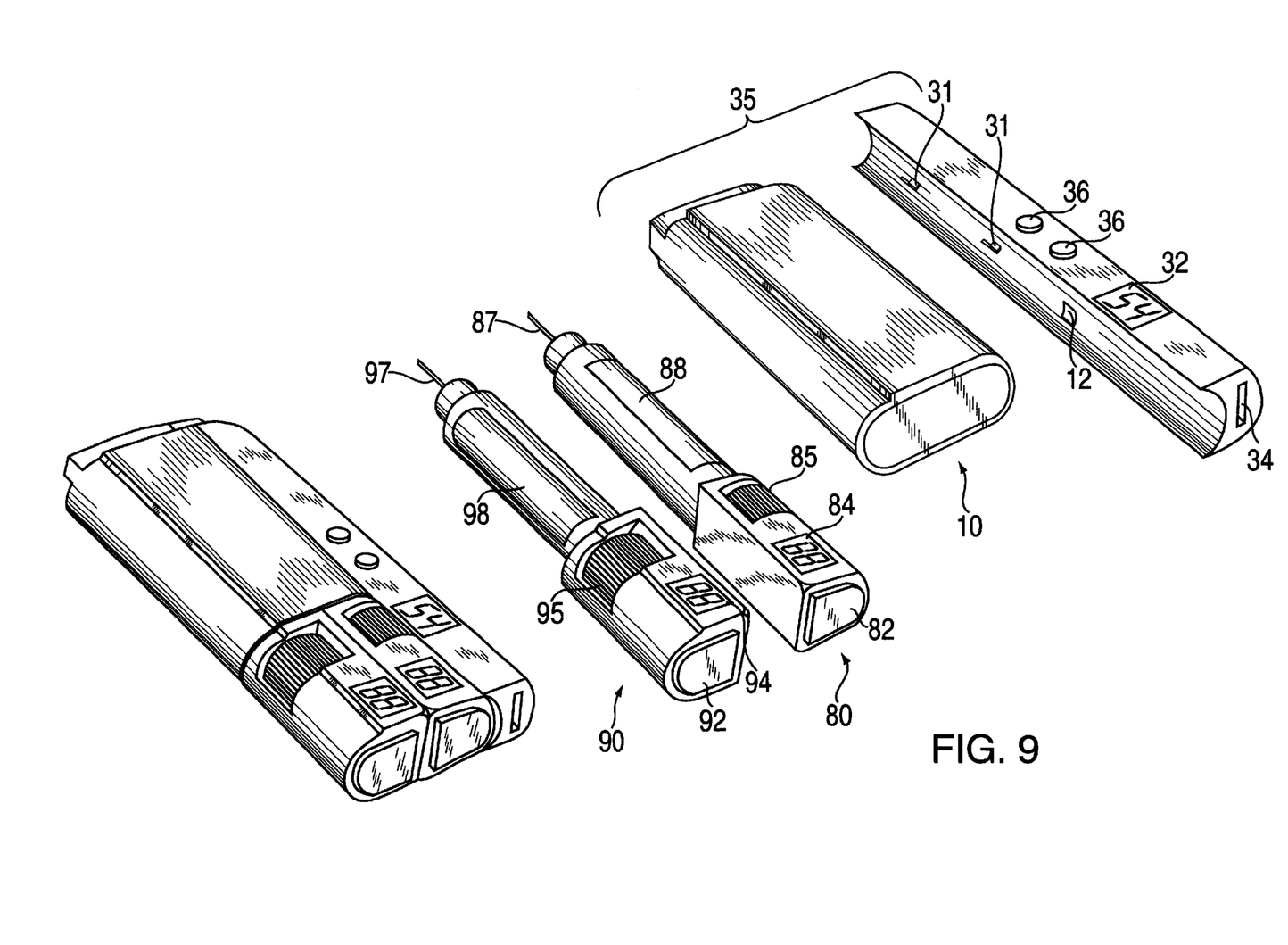

FIG. 4 shows one of the many possible combinations which may be achieved with the apparatus according to the invention. Other examples of expedient combinations are shown in FIGS. 7–9. The combination shown in FIG. 4 has the general advantage that it may induce the user to make some additional blood sugar measurements and possibly regulate with insulin injection when the parts are in an assembled state as one unit. There are also situations in which many blood sugar measurements and injections are required, viz. in connection with so-called insulin analogs which are very rapid action substances, within the order of 10 minutes.

Figure 5:
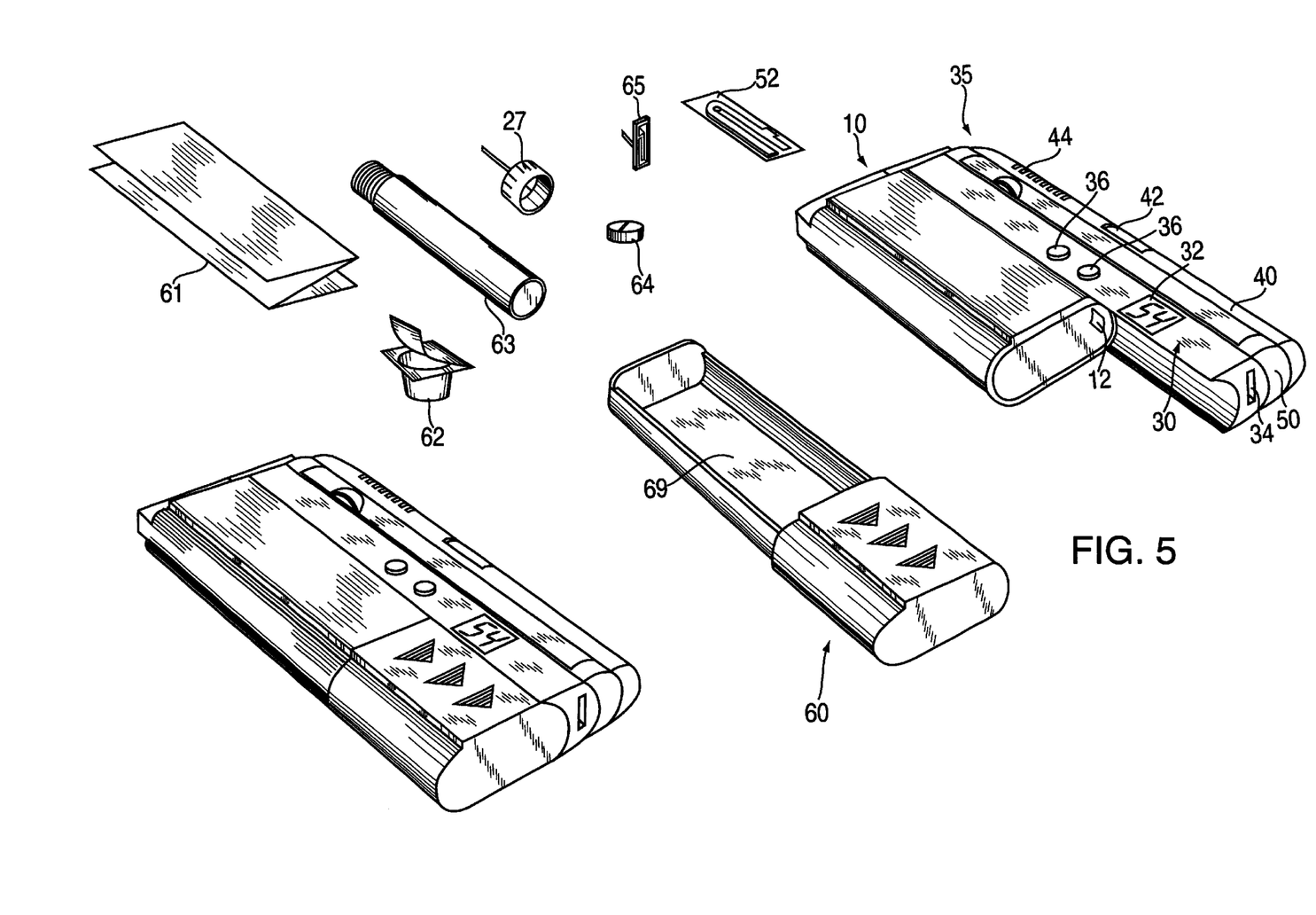
FIG. 5 shows a cap with a BGM, a lancet device, a test strip container and an additional container together with useful/needed extras.

FIG. 5 shows a cap unit 35 that corresponds to the cap unit in FIG. 4. Instead of having a doser 20, there is now provided a container unit 60 with a relative large space 69 for storing the items needed everyday for self-treatment. For a diabetic, e.g. such items could be a napkin 61 for wiping excessive blood after a sample has been taken, a waste container 62 for receiving used items, an extra carpoule 63 which could contain another type of insulin, spare needles 27 for the doser, spare lancets 65 for the lancet device 40, some glucose in the form of glucose tablets 64, etc. In some situations and in certain forms of diabetes, the injection of insulin may be replaced by administration of pills which may be stored in the container, which thus replaces the doser described previously. All these items, or the most relevant ones for a given situation, could be held in the container space 69 for easy retrieval, when needed. Previously the user had to carry a bag for each device (BGM, doser, lancet device, etc.) with the respective accessories. So when the cap unit 35 is fitted to the container unit 60, a single compact, easily portable unit is obtained, which can be customized to meet an individual need for an individual day or situation.

Of course, the individual devices may also be interconnected without the BMG and the doser being coupled together according to the invention. If the doser 20 is not needed—a diabetic does not always need a doser in all situations, since sometimes he only need to observe the glucose level in his blood and regulate this level through a diet—one compact unit with all necessary items readily available is obtained. If a doser 20 is needed, the doser 20 may be fitted with an ordinary cap 10, and thus there will just be two units that contain everything needed in every situation in a very compact and convenient form.

Figure 6:
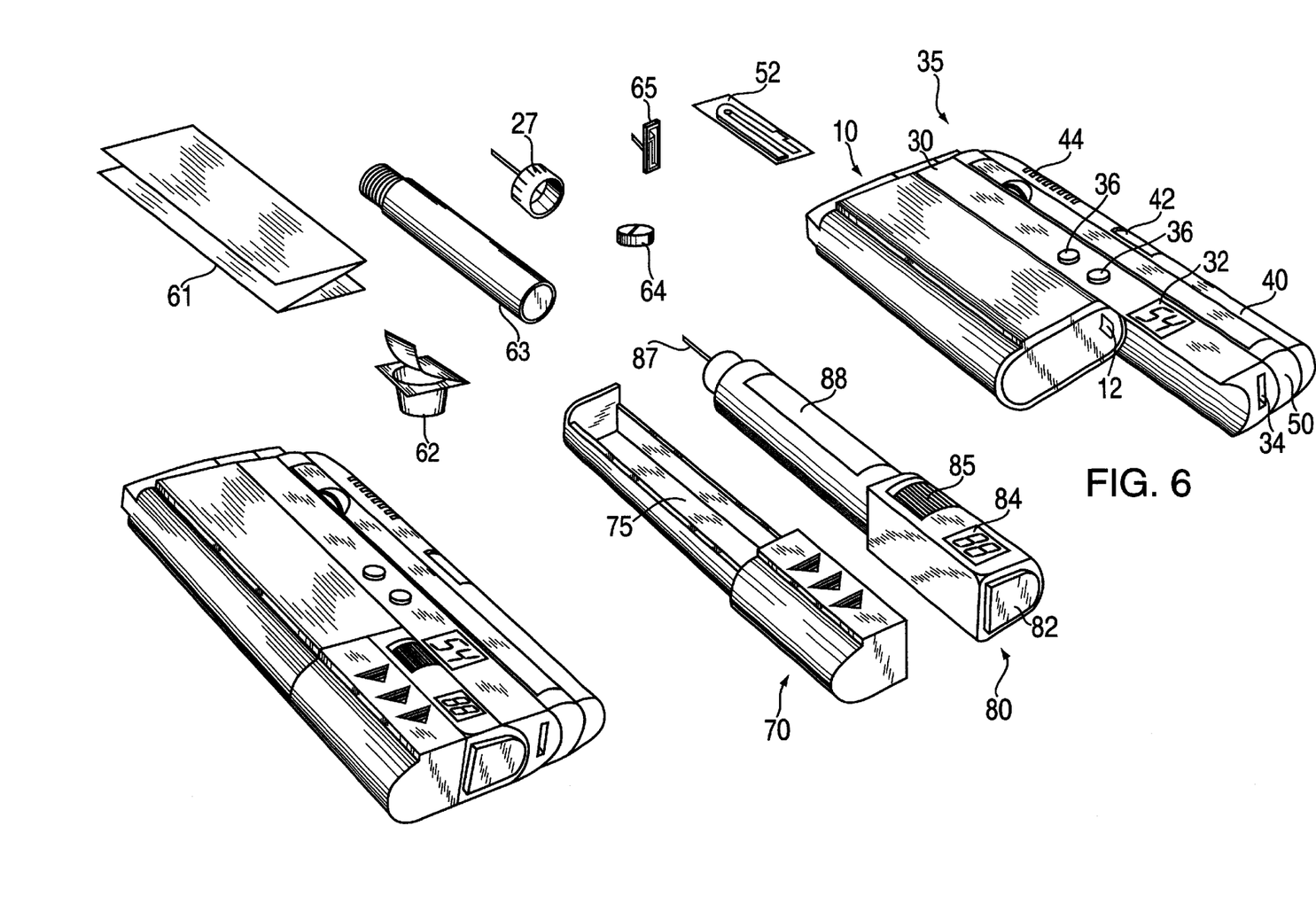
FIG. 6 shows a cap with BGM, a lancet device, a test strip container and a mini-doser and a half-size container together with useful/needed extras.

FIG. 6 shows a cap unit 35 and extras 61–65 and 27 corresponding to the unit and extras in FIG. 5. Also shown is a simple small-sized (e.g. disposable) doser 80 (e.g. an insulin injecting pen) with a turning wheel 85 for adjusting the level/amount of medication to be administered. During the adjustment, a display 84 shows the currently selected amount of medication to be administered. After the appropriate level of medication has been set, the user can press the release button 82, which manually injects/administers the selected amount of medication through the needle 87. The doser 80 further comprises a carpoule (not shown) that contains the medication. The doser 80 has a transparent window 88, so that the amount of medication left in the carpoule readily can be identified. This embodiment also includes a container unit 70, which is half the size of the container unit 60 in FIG. 5. These small size units 70, 80 can be fitted into the cap unit 35 so thereby forming one compact self-treatment unit.

So with this set of modules an optimal compact set can be customized with the things needed for a given situation. The set can either be configured to meet a situation where all the items are needed, thus ending up with two compact units, namely the doser 20 with an ordinary cap 10 and a cap unit 35 with the large container 60 that contains some or all of the extras 61–65 and 27, or be configured to a minimal set containing just items needed for one single situation, e.g. the small doser 80, the half-size container 70 fitted into the cap unit 35 with/without the BGM 30, the lancet device 40 and the test strip container 50, depending on the specific situation.

FIG. 7 shows a combination of the cap 10, the BMG 30 and the storage container 60. Such a combination of devices is relevant e.g. in connection with type 2 diabetics who may take insulin regulating medication in tablet form. Here, the storage container 60 may contain spare lancets 65 (which may belong to another make of lancet devices, which are not shown in the combination in FIG. 7), test strips 52, glucose in the form of glucose tablets 64 and the insulin regulating medication in tablet form. Another use of the combination shown in FIG. 7 is non-refrigerated storage of extra insulin, the temperature then being monitored by the temperature monitoring device 12.

The combination shown in FIG. 8 might be called all in one. The insulin injecting device is replaced by an insulin injecting pen of half the size, which gives room for a container 70 (half as large as the container 60 in FIG. 7).

FIG. 9 shows another possible combination, using two insulin injecting pens so that the user may carry rapid action insulin as well as slow action insulin. One of the pens may also contain one of the very rapid action insulin analogs mentioned above. Clearly, the combination in FIG. 9 may also be supplemented with a lancet device as shown in FIG. 8.

It will now be appreciated that there are many possible combinations which allow the user to combine precisely the equipment he needs in a given situation. In the preferred embodiments, the individual devices are combined side by side, and the storage container and the insulin injecting device are shown in the lateral direction in larger or smaller embodiments. Clearly, an apparatus according to the invention may also comprise devices which may be interconnected and varied in the longitudinal direction.

What is claimed is:

1. A medical apparatus for use by a patient for medical self treatment of diabetes, the treatment including a first operation and at least a second operation, said medical apparatus comprising a first device for performing the first operation and a second device for performing the second operation, wherein said first and said second devices have mutually cooperating coupling means for detachably assembling said first and second devices so as to form a single portable unit, and wherein said first and second devices at least comprise a body fluid analyzer device and a dosing device for administering a predetermined dose of insulin to a patient.

2. The medical apparatus according to claim 1, wherein said body fluid analyzer device is a blood glucose monitor.

3. The medical apparatus according to claim 2, wherein said blood glucose monitor includes a temperature monitoring device located such that, when said blood glucose monitor and insulin injecting device are assembled together, the temperature monitoring device will monitor the temperature of insulin which may be present in said dosing device.

4. The medical apparatus according to claim 2, wherein said medical apparatus includes a cap, and wherein said dosing device comprises two insulin injecting pens arranged to be received as a pair in said cap.

5. The medical apparatus according to claim 2, wherein said medical apparatus includes a cap, and wherein said dosing device comprises an insulin injecting pen and a storage device arranged to be received as a pair in said cap.

6. The medical apparatus according to claim 1, wherein the dosing device is an insulin injecting device.

7. The medical apparatus according to claim 6, wherein said insulin injecting device utilizes a replaceable carpoule of insulin, and wherein said medical apparatus has storage space for storing at least one spare carpoule of insulin.

8. The medical apparatus according to claim 1, wherein said medical apparatus has storage space for storing a supply of lancets for the body fluid analyzer device.

9. The medical apparatus according to claim 1, wherein said medical apparatus has storage space for storing a supply of test strips for said body fluid analyzer device.

10. A medical apparatus for use by a patient for medical self treatment of diabetes, the treatment including analysis of a body fluid, comprising:

a cap having an open end and a cap interior;

a body fluid analyzer coupled to said cap; and at least one additional member having a portion which is selectively insertable into, and removable from, said cap interior, wherein said at least one additional member is selected from the group consisting of an insulin injecting device and a storage container, wherein said cap, body fluid analyzer, and at least one additional member can be assembled to form a single, compact, portable unit.

11. The medical apparatus according to claim 10, wherein said body fluid analyzer and cap are integral with one another.

12. A medical apparatus according to claim 10, wherein said cap and said body fluid analyzer include mutually cooperating elements for detachably coupling said body fluid analyzer to said cap.

13. A medical apparatus according to claim 10, wherein the body fluid analyzer is a blood glucose monitor.

14. A medical apparatus according to claim 10, wherein said at least one additional member is an insulin injecting device.

15. A medical apparatus according to claim 10, further comprising a lancet device, wherein said lancet device and said body fluid analyzer include mutually cooperating elements for detachably coupling said lancet device to said body fluid analyzer, wherein said cap, body fluid analyzer, lancet device, and said at least one additional member can be assembled to form a single, compact, portable unit.

16. A medical apparatus according to claim 15, wherein said cap and said body fluid analyzer include mutually cooperating elements for detachably coupling said body fluid analyzer to said cap, wherein the cooperating elements between said cap and body fluid analyzer include at least one locking member on said body fluid analyzer, and wherein the cooperating elements between said body fluid analyzer and lancet device include at least one said locking member on said lancet device, such that said lancet device may optionally be detachably coupled to said cap.

17. A medical apparatus according to claim 15, further comprising a storage container for storing a supply of lancets for the body fluid analyzer.

18. A medical apparatus according to claim 15, further comprising a storage container, wherein said body fluid analyzer and storage container include mutually cooperating elements for detachably coupling said storage container to said body fluid analyzer, wherein said storage container and lancet device include mutually cooperating elements for detachably coupling said lancet device to said storage container, and wherein said cap, body fluid analyzer, storage container, and at least one additional member can be assembled to form a single, compact, portable unit.

19. A medical apparatus according to claim 18, wherein said cap and said body fluid analyzer include mutually cooperating elements for detachably coupling said body fluid analyzer to said cap, wherein the cooperating elements between said cap and body fluid analyzer include at least one locking member on said body fluid analyzer, and wherein the cooperating elements between said body fluid analyzer and storage container include at least one said locking member on said storage container, such that said storage container may optionally be detachably coupled to said cap.

20. A medical apparatus according to claim 10, wherein said at least one additional member is a storage container providing a storage space which is closed when said storage container is inserted in said cap interior and which is accessible when said storage container is removed from said cap interior.

21. A medical apparatus according to claim 20, wherein said at least one additional member also includes an insulin injecting device, and wherein said storage container and insulin injecting device together have an outer shape which conforms to the shape of said cap interior.

22. A medical apparatus according to claim 10, wherein said at least one additional member includes a pair of insulin injecting devices which together have an outer shape which conforms to the shape of the cap interior.

23. A medical apparatus according to claim 14, wherein said body fluid analyzer includes a temperature monitoring device positioned such that, when said body fluid analyzer is mounted on said cap, and said insulin dispensing device is inserted into said cap, the temperature monitoring device will monitor the temperature of the insulin in the insulin injecting device.

24. A medical apparatus according to claim 12, wherein said cap and said body fluid analyzer include mating surfaces which, in conjunction with said mutually cooperating elements, releasably secure body fluid analyzer to said cap.

25. A medical apparatus according to claim 15, wherein said lancet device and said body fluid analyzer include mating surfaces which, in conjunction with said mutually cooperating elements, releasably secure said lancet device to said body fluid analyzer.

26. A medical apparatus according to claim 18, wherein said storage container, said body fluid analyzer, and said lancet device include mating surfaces which, in conjunction with said mutually cooperating elements, releasably secure said storage container to said body fluid analyzer and said lancet device to said storage container.

* * * * *